United States Patent [19]

Babotai

[11] 4,026,303

[45] May 31, 1977

[54] ENDOCARDIAL PACING ELECTRODE

[75] Inventor: Istvan F. Babotai, Greifensee, Switzerland

[73] Assignee: Vitatron Medical B.V., Dieren, Netherlands

[22] Filed: Nov. 17, 1975

[21] Appl. No.: 632,582

[52] U.S. Cl. .............................. 128/418; 128/419 P
[51] Int. Cl.² .......................................... A61N 1/04
[58] Field of Search ................ 128/404, 418, 419 P

[56] References Cited

UNITED STATES PATENTS

| 3,472,234 | 10/1969 | Tachick | 128/419 P |
| 3,485,247 | 12/1969 | Ackerman | 128/419 P |
| 3,911,928 | 10/1975 | Lagergren | 128/419 P |

FOREIGN PATENTS OR APPLICATIONS

| 1,277,107 | 6/1972 | United Kingdom | 128/419 P |

OTHER PUBLICATIONS

Berens et al., "American Journal of Cardiology" vol. 34, Sept. 1974, pp. 325–332.

*Primary Examiner*—William E. Kamm
*Attorney, Agent, or Firm*—Woodcock Washburn Kurtz & Mackiewicz

[57] ABSTRACT

An endocardial pacing electrode adapted to be screwed under the inner muscles of the heart in order to be fixed in stimulating contact with the same, the electrode having a spiraled or helically wound tip which is rounded so that the tip engages but does not enter the trabaeculae. A portion of the electrode tip may be covered with an insulating material, leaving a predetermined portion which constitutes the stimulating surface area. The length of the electrode proximal to the tip is hollow to permit insertion of a mandrin, for rotating the electrode around the mandrin and positioning the tip for optimum contact for low stimulation threshold.

13 Claims, 7 Drawing Figures

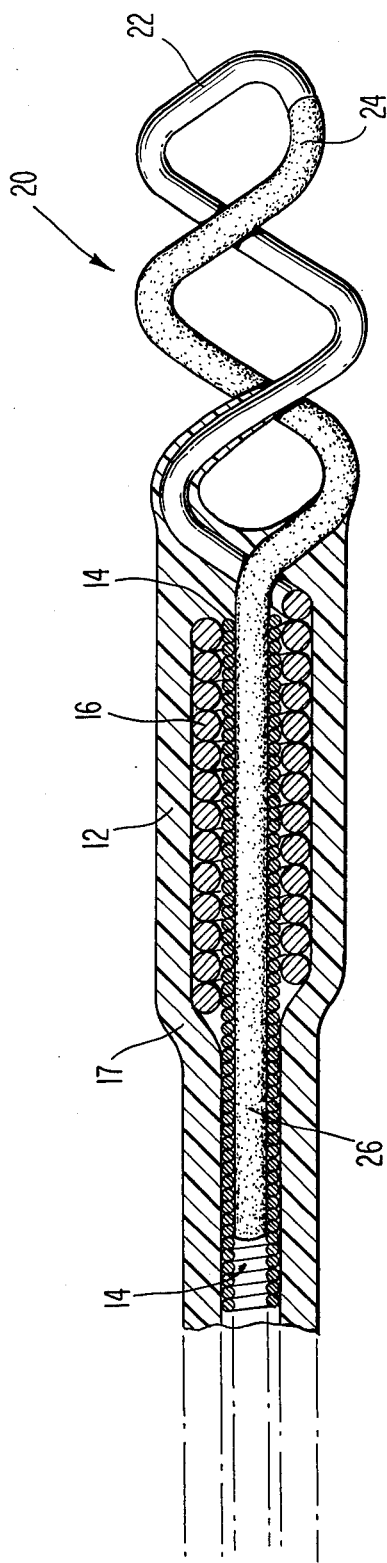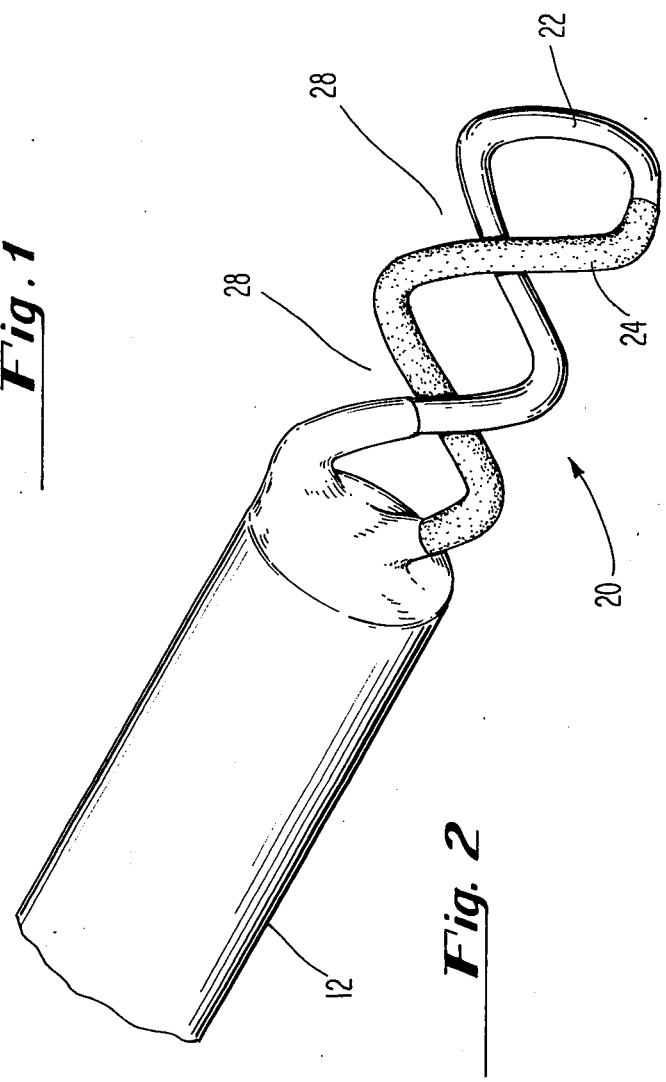

ENDOCARDIAL PACING ELECTRODE

BACKGROUND OF THE INVENTION

1. Field of the Invention

This invention lies in the field of cardiac pacing apparatus and, more particularly, in the area of electrodes, of catheters, used in a cardiac pacing system, for delivering stimulating signals generated by an electronic pacer to the heart.

2. Description of the Prior Art

This specification discloses an electrode as used in cardiac pacing. In much of the literature, the term catheter is employed to describe the same apparatus. For example, the electrode of this invention may also be suitably described as a unilateral catheter having a single electrode, in which description the term electrode would refer to the stimulating tip. In this specification, the term electrode is used with the same meaning as catheter, referring to the entire device for conducting stimulating pulses.

A chronic problem with electrodes as used in cardiac pacing is proper fixation of the distal tip within the heart so that good contact is made with the inner lining of the heart, which is necessary to provide good pacing. The term fixating is used to describe the procedure of fixing the electrode tip relative to the inner lining of the heart so that proper stimulation is assured with reasonable permanency. In the case of ventricular pacing, it is known that the stimulating contact element cannot be loosely positioned within the ventricle, but must be fixed against or at least within a minimum distance from the endocardium. Another important reason for obtaining good fixation is so that the threshold for stimulation remains substantially constant throughout the lifetime of electrode usage. Clearly, if the distal stimulating contact is permitted to shift in position relative to the endocardium, the threshold will likewise shift, with potentially disasterous results.

In the prior art, a large number of fixation type designs have been utilized, generally with indifferent success. In some endocardial electrodes, the design is such that the blood can work itself into the electrode and thus block the fixation mechanism. Another disadvantage of most fixation systems is that they pierce or grasp the endocardium so as to cause physical damage. This is particularly serious for atrial electrodes, due to the thin atrial walls. There exist a number of issued patents describing electrodes designed to screw into the heart tissue. However, there has remained a great need in this art for an endocardial catheter which can be safely and securely positioned so as to provide the physician with means for obtaining an optimally low threshold, and which will minimize damage to the endocardium both at time of insertion and later.

SUMMARY OF THE INVENTION

It is a primary objective of this invention to provide electrode apparatus adapted to engage the inner lining of a patient's heart without piercing it, so as to enable speedy and stable fixation for cardiac pacing.

It is a further objective of this invention to provide an electrode having a distal portion formed so as to provide openings designed to interact with the trabaeculae in a manner such that the stimulating contact can be screwed to an optimal position, so as to provide means for stable low threshold pacing.

In accordance with the above objectives, there is disclosed an endocardial pacing electrode adapted with a specially configured spiral or helically wound tip, the tip being closed upon itself or otherwise configured so that it has no sharp points and is not inserted into the endocardium. The spiral configuration provides open grooves such that the cardiac muscles on the inside of the heart can be worked within such grooves by turning of the electrode at time of insertion. In this manner, the tip is screwed, or rotated until the caridac muscle lays in close contact with the stimulating surface or tip of the electrode, thereby providing optimal patient stimulating threshold conditions. A predetermined portion of the spiral pacing tip may be insulated, leaving a second predetermined portion which acts as the actual pacing contact, thereby providing a desirable amount of pacing surface which is reliably placed in contact with the heart muscle. The main length of the electrode suitably comprises an axially hollow lead which connects to the pacing contact at the distal end and to a pacing generator at the proximal end, and which permits insertion of a cardiac through the center thereof, allowing twisting or rotating manipulation of the electrode at the proximal end in order to properly position the electrode within the heart.

BRIEF DESCRIPTION OF THE DRAWINGS

FIG. 1 is a detailed view, partly in cross section, of the distal end of a first embodiment of the pacing electrode of this invention.

FIG. 2 is a perspective view of the embodiment of FIG. 1, looking at the end of the electrode tip from an acute angle.

DESCRIPTION OF THE PREFERRED EMBODIMENT

Figure 3:
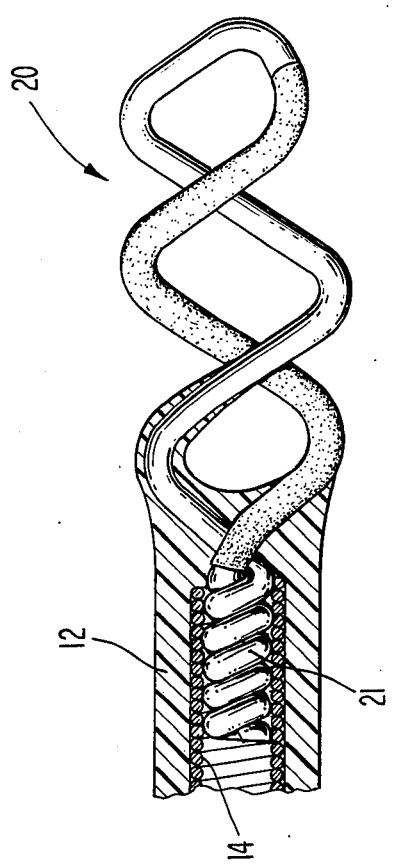
FIG. 3 is a detailed view, partly in cross section, of the distal end of another embodiment of the pacing electrode of this invention.

Referring now to FIG. 1, there is shown a detailed view of the proximal end portion of a first embodiment of the electrode of this invention. The main length of the electrode is contained within a tube or casing 12 of Teflon or other suitable material, as illustrated also in FIG. 4. A lead, or conductor 14 in spiral form extends the length of the catheter, terminating at the distal portion as shown in FIG. 1. In the embodiment of FIG. 1, a second spiral, or helical coil 16 is positioned surrounding the conductor 14, and in close electrical contact therewith, both conductors 14 and 16 at this point being tightly encased by outer tube 12. The tube 14, at the distal end shown in FIG. 1, has a shoulder 17 which permits enclosure of additional coil 16 as well as conductor 14. Coil 16 is extended outside of casing 12 to form the spiral pacing contact 20. As shown in FIG. 1, spiral contact 20 extends for approximately 1½ loops or cycles, to the far distal end where it turns and coils back through a like distance and extends through the center of conductor 14, the extended portion being designated as 26. Portion 26 may additionally be soldered or otherwise connected to coil 14, to ensure electrical contact between the spiral portion 20 and the conductor 14. The casing 12 extends over the distal end, as shownn at 13, sealing off the remainder of the electrode from the spiral tip.

The configuration of spiral portion 20 is seen in perspective form in FIG. 2 which illustrates the open type structure of the contact which permits close insertion of the contact into the muscle tissue, or trabaeculae. It is seen that the contact tip is not sharp, has no end points, but rather is round, continuous, and closes upon itself in a closed spiral configuration, with open grooves 28. The tip has a configuration such that it can be screwed under the trabaeculae or inner muscles of the heart, in either the ventricle or atrium. Thus, what is provided is an electrode tip which is adapted to interface with the trabaeculae in a maximum-contact relationship, thereby ensuring optimal threshold for pacing.

Referring to FIG. 3, there is shown an alternate embodiment of the invention without the shoulder portion shown in FIG. 2. In this embodiment, the contact portion 20 which extends beyond the end of casing 12 is substantially in the same spiral form as shown in FIG. 1. The tip has a tightly wound portion 21 which is forced into the proximal end of conductor 14, where it is held in tight mechanical and electrical contact with conductor 14.

It has been determined that it is desirable that the surface of the contacting tip of the catheter be preferably about 10–15 mm$^2$. At the same time, the contact tip portion must have enough turns to provide the open spaces to optimize contact between the tip and the trabaeculae. If the conductor wire of which the spiral is made is 0.5 mm thick, a single turn of such wire has a surface of about 14 mm$^2$. Accordingly, for the configuration as shown in FIG. 1, a portion of the spiral tip is insulated preferably so that the remaining exposed portion extends a full loop, or the length of the tip for a longer contact tip. As shown, insulating material 24 is provided substantially from the far end portion of the looped tip along one path back to the encased portion of the catheter. With this design, substantially the entire length of the tip has an uninsulated or conductive portion, such that if the muscle tissue is positioned into any of the open grooves within the spiral, it will be in contact with a conductive portion of the catheter tip. The tip insulation coating is suitably comprised of a material such as Teflon, polyetheen, polyamide, polytetrafluorathyleen, fluorethylpropyleen, silicon rubber, and other like materials. The thickness of the insulation is suitably about 50 microns. The material of the helically wound wire forming the spiral shaped tip can be platinum, platinum-iridium, elgiloy, or any other non-toxic conductive material.

Figure 4:
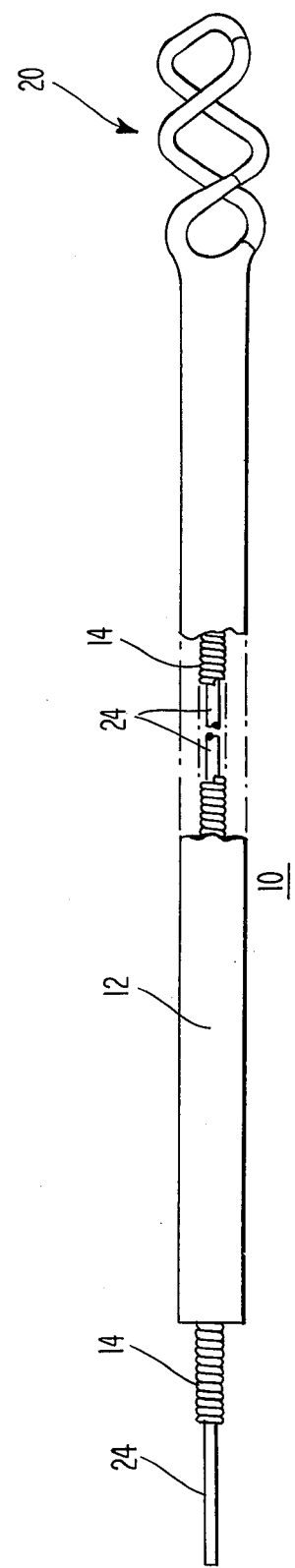
FIG. 4 is a diagrammatic sketch of the entire electrode, with a cut away portion showing the position of the mandrin within the electrode.

Referring to FIG. 4, there is shown a diagrammatic view of the overall electrode of this invention. The electrode 10 suitably has extending therethrough a mandrin or stylet 24, which is positioned axially within the helical conductor 14. Conductor 14 need not be of a helical configuration, but could be either some other configuration of hollow conductor or even a solid conductor. However, in order to utilize the advantage provided by a mandrin, it is suitable and preferred that conductor 14 be hollow, as in the helical configuration shown. The mandrin extends substantially to the end portion of the electrode, terminating just proximal of the tip 20. With this configuration, the pacing surface 22 can very easily be fixated within the heart by turning the proximal end of the electrode clockwise, thereby screwing or rotating the distal end under the endocardial muscle. The open structure of the spiral tip permits entry of the trabaeculae within the tip, providing efficient placement and fixation and also establishing an environment for fast ingrowing of the heart tissue within the tip, such that permanent fixation is achieved rapidly. As can be seen, the open structure of the spiral tip permits the cardiac muscles to work themselves between the turns when the electrode is rotated, such that the muscles lay in close contact with the stimulating surface. In contrast to other fixation mechanisms, the pacing electrode of this invention does not damage the endocardium, and consequently causes reduced tissue reaction. Also, due to the close contact which is made, the chronic or long term pacing threshold can be established at an optimally low level. An additional advantage of the electrode of this invention arises from the absence of any sharp parts, such that the electrode can be inserted into the patient's cardiovascular system without the need of any protecting tube or other device.

While the preferred embodiments of this invention have been illustrated as shown in the drawings and described hereinabove, it is to be understood that variations may be adopted using the essential features of the invention. For example, the spiral stimulating tip may comprise a conventional length as well as a spiral shaped shoulder immediately therebehind, or any other configuration comprising spiral loops. The number of loops in the spiral, as well as the pitch and diameter thereof, may be modified as, for example, for use in the ventricle and atrium respectively. The insulation on a portion of the tip is optional, and need not be used for some tip configuration. Further, in the manufacture of the catheter, the spiral tip may be initially positioned just inside of the casing 12, and upon insertion of the distal end of the catheter into the patient's heart, the tip may be pushed out of the casing by forward pressure applied through the stylet. with this embodiment, the tip may be initially formed such that when it is freed from the constraint of the casing it expands slightly, thereby achieving a diameter in excess of the diameter of the casing. In another arrangement, the tip may be rotatable relative to the casing, with the mandrin being keyed into the tip so that the physician rotates the mandrin so as to rotate the tip.

Figure 5:
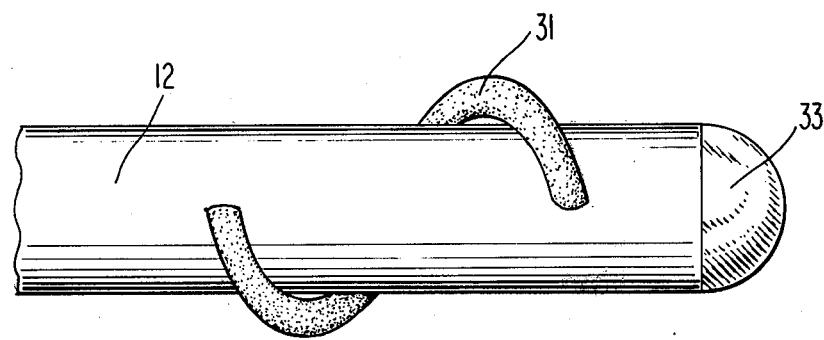
FIG. 5 is a diagrammatic view of the distal end of a shouldered embodiment of the pacing electrode of this invention.
Figure 6:
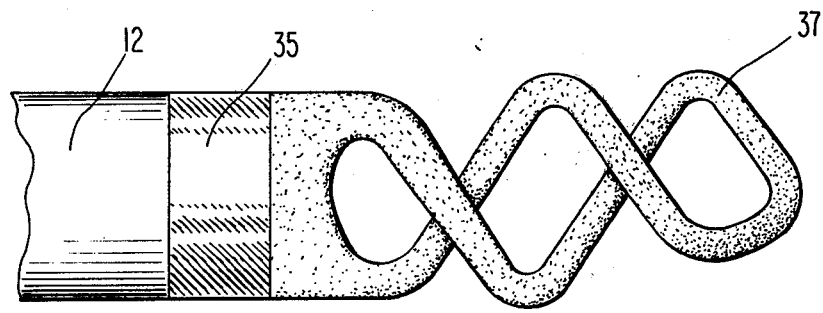
FIG. 6 is a diagrammatic view of yet another embodiment of the pacing electrode of this invention.
Figure 7:
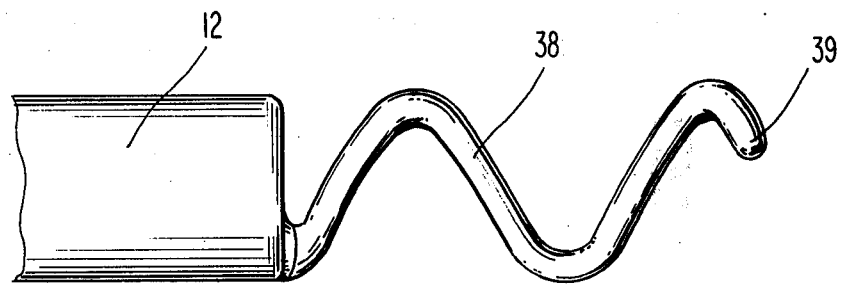
FIG. 7 is a diagrammatic view of an embodiment of the pacing electrode of this invention, wherein the stimulating contact has a rounded tip, and does not close on itself.

FIGS. 5, 6 and 7 illustrate some of the alternate embodiments of the invention. In FIG. 5, an insulated spiral loop 31 is located just proximal of the distal stimulating tip 33. In this configuration, the fixating and stimulating mechanisms are separated, with loop portion 31 serving the fixation function, while tip 33 is a conventional type of stimulating contact tip. In FIG 6, there is shown a configuration where a looped portion 37 is placed at the far distal end, and a stimulating ring 35 is positioned proximal thereto. Again, in this configuration the fixation and stimulating portions are separated, but their relative positions are reversed as compared to the configuration of FIG. 6.

The configuration of FIG. 7 shows a spiral tip which does not close upon itself, but rather terminates with a rounded surface 39. It is in fact a modification of the configuration of FIG. 5, with the casing 12 stopping where the spiral loop starts, the spiral loop being connected to conductor 14 and rounded portion 39. As used herein, rounded means without any sharp or blunt edge, such that a rounded tip or contact element is defined as one with no sharp or blunt edge on any part thereof. This configuration is more suitable for temporary pacing applications, since the tip may be more easily withdrawn by reverse screwing, even after ingrowing tissue has appeared.

In all of the embodiments illustrated, better contact can be achieved by screwing the electrode after insertion into the heart, the screwing or rotating operation being continued until a good threshold position is achieved. As the physician turns the electrode, the spiral tip advances through and between the trabaeculae, without actually penetrating, and threshold is monitored. The procedure continues until there is confidence that the optimum position for good threshold has been obtained. The positioning is then stopped, with the entire tip in optimal position without the endocardium, that is, with none of it mechanically inserted into the endocardium. The fact that there is no insertion provides the added advantage that there is reduced mechanical or physical damage of the endocardium, which permits a lower steady state threshold when fixation is achieved.

I claim:

1. A pacing electrode adapted for insertion through a portion of a patient's cardiovascular system such that its distal end is within the patient's heart, comprising a lead extending substantially the length of such electrode, and a contact tip element positioned at the distal end of said catheter and electrically connected to said lead, said tip element being of a closed spiral configuration having a rounded surface and presenting a plurality of open grooves.

2. The electrode as described in claim 1, wherein said contact tip element has a first portion thereof covered with insulation, and a second portion of said tip has a conductive surface.

3. The electrode as described in claim 2, wherein said conductive surface extends substantially the length of said tip element.

4. The electrode as described in claim 3, wherein said first insulated portion extends substantially the length of said tip element.

5. The electrode described in claim 2, wherein said tip insulation is about 50 microns in thickness.

6. The electrode as described in claim 1, wherein said conductive surface is about 10 to 15 mm².

7. The electrode as described in claim 1, wherein said lead is helical in form, thereby providing a hollow axial space within said lead.

8. The electrode as described in claim 7, comprising a mandrin extending substantially the length of said lead.

9. A stimulating electrode adapted for transmission of stimulating signals to a body organ, comprising:
   a. a lead extending substantially the length of the electrode, from a proximal end where stimulus signals may be connected to a distal end where such stimulus signals are delivered to said body organ; and
   b. contact means located at said distal end, connected to said lead, for engaging said organ so that said stimulus signals can be delivered thereto, said contact means having a closed spiral configuration and including a first portion characterized by having a conductive surface and extending substantially the full length of said contact means and a second portion mechanically and electrically continuous with said first portion having an insulating covering over at least a part thereof.

10. The electrode as described in claim 9, wherein said second portion comprises a spiral length extending substantially the full length of said contact means.

11. The electrode as described in claim 10, wherein said insulating covering covers substantially all of said second portion.

12. A pacing electrode for delivering stimulus signals to the inner muscles of a patient's heart, said electrode being adapted to be engageable with said heart muscles without penetrating same, cmprising:

a conducting lead extending substantially the length of said electrode, the lead being covered with an insulating casing; and contact tip means electrically integral with said lead, for delivering said stimulus signals to said heart muscles and for providing a plurality of open grooves, said grooves being adapted to interface with said heart muscles, said tip means having a closed spiral configuration and respective insulated and uninsulated portions which together define said plurality of open grooves.

13. The pacing electrode as described in claim 12, wherein said tip means is a continuous element having a closed spiral configuration with a fixed overall length, and wherein said insulated and uninsulated portions extend commonly through at least a predetermined distance of said overall length.

* * * * *

UNITED STATES PATENT AND TRADEMARK OFFICE
CERTIFICATE OF CORRECTION

PATENT NO. : 4,026,303
DATED : May 31, 1977
INVENTOR(S) : Istvan F. Babotai

It is certified that error appears in the above-identified patent and that said Letters Patent are hereby corrected as shown below:

Column 2, line 22, delete "cardiac" and insert therefor
--mandrin--.

Signed and Sealed this twenty-third Day of August 1977

[SEAL]

Attest:

RUTH C. MASON
Attesting Officer

C. MARSHALL DANN
Commissioner of Patents and Trademark